United States Patent [19]

Weinges et al.

[11] 4,401,825
[45] Aug. 30, 1983

[54] REACTIVE IRIDOID DERIVATIVES; PROCESS FOR MANUFACTURE AND APPLICATION OF SAME

[75] Inventors: Klaus Weinges, Heidelberg; Herbert von der Eltz, Plankstadt; Hermann Jaggy, Bad Schönborn, all of Fed. Rep. of Germany

[73] Assignee: Willmar Schwabe GmbH & Co., Karlsruhe, Fed. Rep. of Germany

[21] Appl. No.: 285,989

[22] Filed: Jul. 23, 1981

[30] Foreign Application Priority Data

Aug. 12, 1980 [DE] Fed. Rep. of Germany ....... 3030477

[51] Int. Cl.³ .................. C07D 309/12; C07D 311/94
[52] U.S. Cl. ...................... 549/396; 560/121; 562/503
[58] Field of Search ...................... 260/345.2; 549/396

[56] References Cited

U.S. PATENT DOCUMENTS 3,089,877  5/1963  Korte et al. .................. 549/396

OTHER PUBLICATIONS

Weinges et al., Angew. Chem., 92, 639 (1980).

McOmie, Adv. in Org. Chem., vol. 3, 1963, Interscience Publ., London, pp. 216-225.

*Primary Examiner*—Nicky Chan
*Attorney, Agent, or Firm*—Toren, McGeady and Stanger

[57] ABSTRACT

Reactive iridoid derivates represented by the following general formula

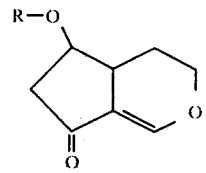

(wherein R represents a hydrogen atom, an alkyl group with 1 to 5 carbon atoms, an acyl group with 2 to 6 C atoms, an unsubstituted aralkyl group with 7 to 12 C atoms, a methanesulfonyl- or toluenesulfonyl group, a benzoyl-, a preferably para-substituted nitrobenzoyl- or chlorobenzoyl group, or a tetrahydropyranyl group), process for the manufacture of said derivatives starting from catapol as an easily obtainable natural substance and use of said derivatives as intermediates for the manufacture of prostanoids.

4 Claims, No Drawings

REACTIVE IRIDOID DERIVATIVES; PROCESS FOR MANUFACTURE AND APPLICATION OF SAME

BACKGROUND OF THE INVENTION

1. Field of the Invention

The invention concerns reactive iridoid derivatives of the general formula I

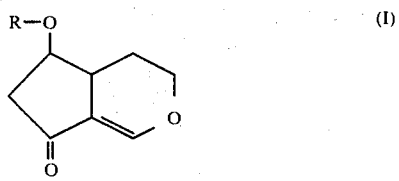

wherein R is a hydrogen atom, an alkyl group with 1 to 5 carbon atoms, an acyl group with 2 to 6 C atoms, an unsubstituted aralkyl group with 7 to 12 C atoms, a methanesulfonyl- or toluenesulfonyl group, a benzoyl-, a preferably para-substituted nitrobenzoyl- or chlorobenzoyl group or a tetrahydropyranyl group.

2. Description of the Prior Art

The iridoids are a group of natural substances whose common structural feature consists of the cyclopentanpyran ring system:

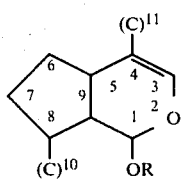

The iridoids occurring in nature are generally present in the form of glycosides, wherein their sugar is linked with the $C^1$-atom of the iridoid. An iridoid glycoside which can be isolated easily from the drug Picrorhiza kurrooa, Royle (Indian Gentian, family Scrophulariaceae) is the Catalpol of formula II

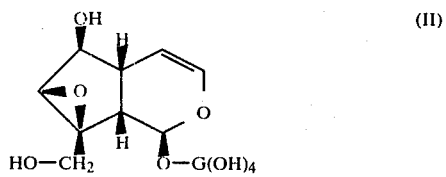

$(-O-G(OH)_4 = 1-\beta\text{-D-Glucopyranosyl rest})$ which is characterized by the epoxide ring between $C^7$ and $C^8$ and is present as 1-β-D-glucopyranoside.

A survey of the iridoid glycosides and their isolation is to be found in the article of O. Sticher and U.Junod-Busch in: Pharm.Acta Helv. 50, pp. 127–144 (1975).

It is the aim of this invention to provide the compounds of general formula I and the simplest possible procedure for their manufacture, thus also providing a new and simple access to reactive iridoid derivatives, in order to open up in this manner new ways of synthesizing pharmacologically effective classes of natural substances, prostanoids in particular.

SUMMARY OF THE INVENTION

This aim is achieved by the preparation of the compounds of the invention, the process according to the invention and the application of these compounds resulting from the invention.

The compounds 7-hydroxy-3-oxa-bicyclo[4.3.0]non-1-en -9-one and 7-acetoxy-3-oxa-bicyclo[4.3.0]non-1-en -9-one, which may be present on account of their asymmetrical carbon atoms $C^6$ and $C^7$ in the form of their optically active(+)- and (−)-diastereomeres, or in the form of their racemates, are particularly preferred in the case of the invention.

With regard to the nomenclature of the compounds of the invention, attention must be given to the fact that the numbering of the ring system differs according to whether it is designated as an iridoid derivative or a bicyclo[4.3.0]nonenone:

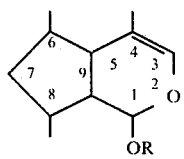 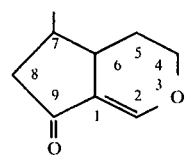

Iridoid numbering    Bicyclo[4.3.0]nonenone numbering

The compounds of General Formula I according to the invention can be manufactured from natural Catalpol (1a) without timeconsuming separation processes in four or five reaction steps according to the following reaction scheme:

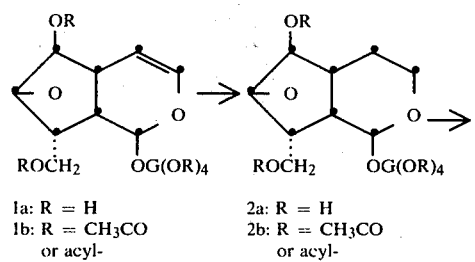

1a: R = H
1b: R = CH₃CO or acyl-

2a: R = H
2b: R = CH₃CO or acyl-

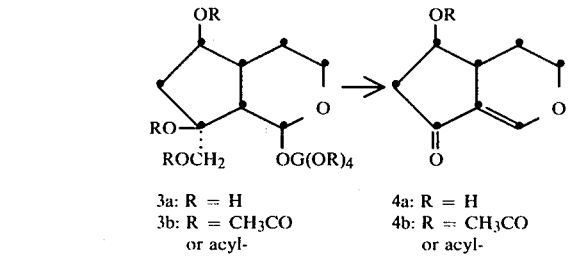

3a: R = H
3b: R = CH₃CO or acyl-

4a: R = H
4b: R = CH₃CO or acyl- (acyl is alkanoyl with 2 to 6 carbon atoms)

DESCRIPTION OF THE PREFERRED EMBODIMENTS

In the first reaction step, Catalpol is acylated (O-acylation) with the anhydride of a carbonic acid possessing 2 to 6 carbon atoms, in anhydrous pyridine at ambient temperature to obtain hexa-acyl-catalpol (1b). In this process, the four free hydroxyl groups of the β-D-glucopyranose are also O-acylated.

In the second reaction step, the resultant hexaacyl-catalpol (1b) is quantitatively converted by catalytic hydrogenation to the corresponding saturated compound, i.e. hexaacyl-dihydrocatalpol (2b).

The hexaacyl-dihydrocatalpol (2b) is then, in the third reaction step, converted by reaction with lithium alanate in a dipolar, aprotic solvent, preferably in absolute tetrahydrofurane, whereby the epoxide ring is split regio-selectively and all acyl residues are once more split off, thus producing 6,8-dihydroxy-8-hydroxymethyl-1-iridanyl-1'-β-D-glucopyranoside (3a).

In the fourth reaction step, the compound (3a) is oxidized with an oxidizing agent known for splitting glycols, preferably with periodic acid or one of its salts, especially with sodium periodate, or with lead tetraacetate, preferably in an aqueous solution, where after the reaction solution is saturated with a weak base, for example aqueous solution of hydrogen carbonate. The final step in the procedure is remarkable in that the oxidation, for example with sodium periodate in the case of the iridoid glucosides, normally causes the glucoside bond—contrary to the other glucosides—to be split, so that the aglycone forms are also obtained apart from the carbonic acids produced from the glucose. When compared with the known acid-catalyzed glucoside splitting, this has the advantage that the aglycones can be isolated from the weak alkaline solution using a suitable base directly following saturation, and do not have to be separated from the glucose otherwise produced. Surprisingly, however, in the oxidative splitting of compound (3a), we do not obtain the aglycone but, directly, the compound (6R. 7R)-(−)-7-hydroxy-3-oxa-bicyclo[4.3.0]non-1-en -9-one (4a), as water is simultaneously split off after the breaking up of the glucoside bond in the weak alkaline medium.

In the fifth reaction step, the compound (4a) is alkylated, acylated or condensed using methods more or less generally known in order to obtain, as required, the desired O-substituted derivatives of general formula I. The acylation of the 7-hydroxyl group of compound (4a) is performed with the corresponding carbonic acid anhydride or carbonic acid halogenide, for example with acetic anhydride, benzoyl chloride, p-nitrobenzoylchloride, methanesulfonyl chloride, toluenesulfochloride etc. Alkylation is performed in a corresponding manner using an alkyl halogenide with 1 to 5 carbon atoms, for example with ethyl bromide, with an aralkyl halogenide, for example benzyl chloride, with an alkyl sulphate or alkyl-p-toluene sulfonate. Condensation can be realized with every suitable compound, for example with tetrahydropyrane.

The compounds according to the invention can be used in a particularly advantageous manner as reactive intermediate products for the synthesis or the partial synthesis of natural substances, particularly of prostanoids.

It is known that the prostanoids or prostaglandins are counted as tissue hormones and exhibit a wide range of pharmacological efficacity. In particular, they have an effect on the smooth muscle tissue and on circulatory processes, are local modulators of hormonal effects, stimulate the secretion of prolactin, and take part in haemostasis as well as immunological resistance mechanisms. All mammal cells are capable of synthesizing prostaglandins. They are released by a large number of physiological, pharmacological and pathological stimuli.

H. König in: Klinische Wochenschrift

Vol. 53, pp. 1041-1048 (1975) provides a short summary on the chemistry and the metabolism of prostaglandins.

The compounds provided by the invention open up a new and chemically original method of synthesis leading to prostanoids, which are of extreme pharmacological importance; the initial steps of this process are obtained from the following formula scheme:

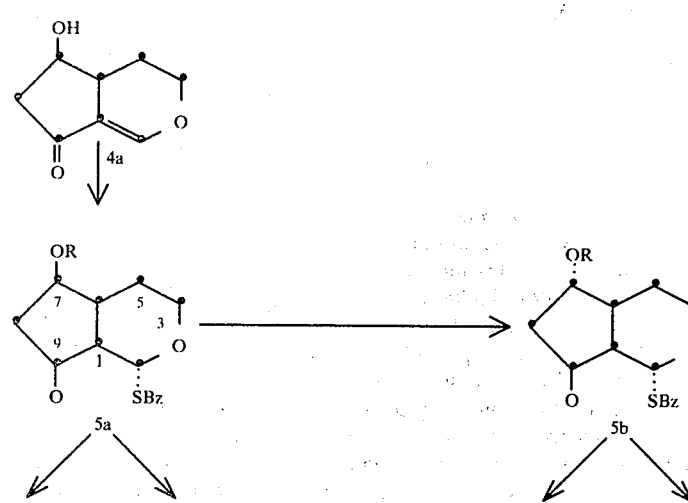

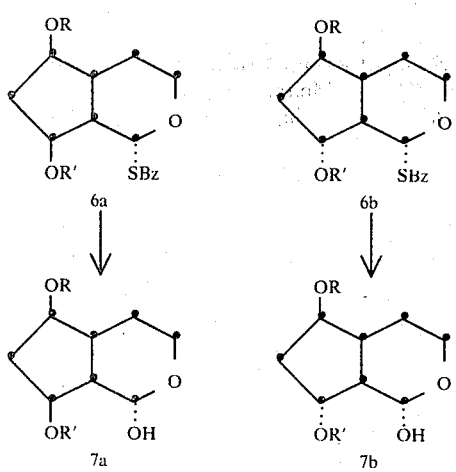
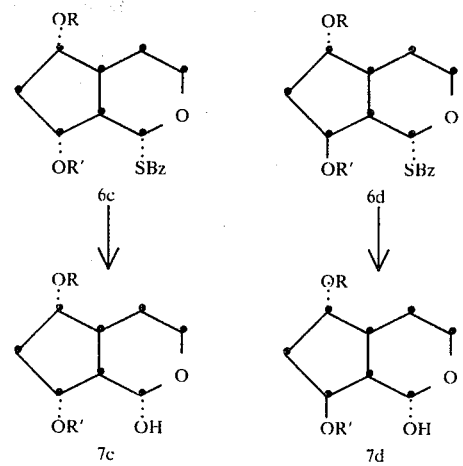

In the first reaction step, benzylmercaptan or another suitable nucleophil, for example the N≡C-group, is added to the double bond of the ketoenolether (4a). The addition of benzylmercaptan results in the formation of 1-benzylthio-7-hydroxy-3-oxa-bicyclo[4.3.0]nonan -9-one (5a). (Hereinafter, the symbol 'SBz' means a compound having a benzyl group attached to the sulfur. The reaction step 4 for the production of the keto-enolether (4a) and the addition of benzylmercaptan can advantageously be performed in one procedure, directly following each other.

In the second reaction step, the compound (5a) is reduced with sodium borohydride to form (7R, 9S)-(−)-1-benzylthio-7,9-dihydroxy-3-oxa-bicyclo[4.3.0-]nonane (6a) (Main Product) and to the (7R, 9R)-diastereomer (6b) (By-product). The diastereomers are quantitatively separated by column chromatography. The reaction may also be performed stereoselectively, so that only compound (6a) is formed (compare E. Martinez, J. M. Muchowski and E. Velade in: Journal of Organic Chemistry Vol. 42, p. 1087 (1977)).

The benzylthio groups of the compounds formed can be split off quantitatively using mercury acetate, whereby the corresponding 2,7,9-trihydroxy-3-oxa-bicyclo[4.3.0]nonanes (7a) and (7b) are produced.

The stereoisomeric series of compounds (5b), (6c), (6d) (7c) and (7d) are obtained by inverting the hydroxyl group on the C⁷-atom of compound (5a), this being in accordance with the procedure described by H. Loibner and E. Zbiral in Helv. Chim. Acta Vol. 59, p. 2100 (1976). The further reactions of compound (5b) to form compounds (7c) and (7d) are performed analogously to the reaction steps 2 and 3 described above.

The further reaction of compounds (7a) through (7d) to produce prostanoids is performed in accordance with the following formula scheme:

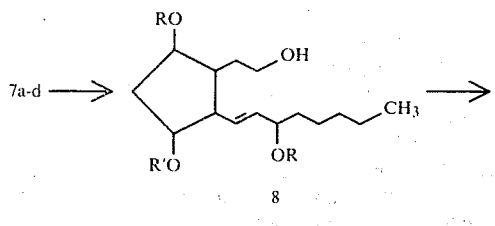

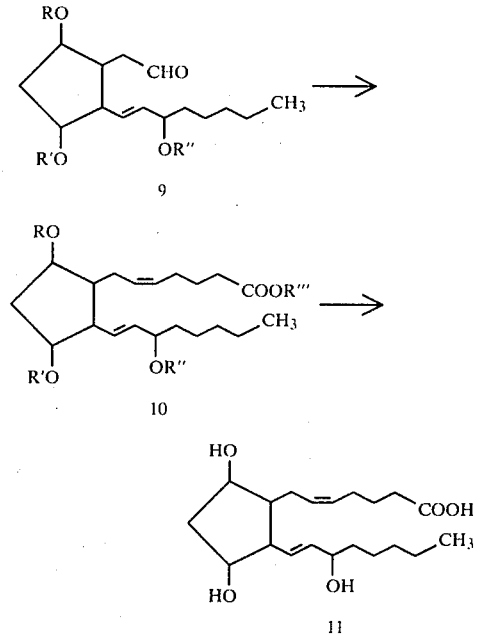

In this case, the hemiacetals (7a) through (7d) are converted to form compound (8) with the by (7a) through (7d) pre-defined configuration using the relevant Wittig reagent, i.e. with correspondingly substituted monoalkyl-triphenyl-phosphonium salts (compare E. J. Corey et al. in: Journal of the American Chemical Society Vol. 93, p. 1490 (1971)). The primary hydroxyl group produced by the splitting of the pyran ring system in subsequently oxidized to aldehyde (9) with pyridinium dichromate (PDC) (comp. Tetrahedron Lett. 1979, 399) or with pyridinium chlorochromate (PCC) (comp. Tetrahedron Letters 1975, 2647). The second side chain of the prostanoid desired is, in its turn, also linked to compound (9) by means of a Wittig reaction (Wittig reagent: comp. J. S. Bindra and R. Bindra, Prostaglandin Synthesis, Academic Press, Inc., New York, 1977, p. 210). Finally, the protective groups R,R', R" and R''', for example acetyl-, benzyl-, benzoyl, p-nitrobenzoyl-, mesyl- and tosyl-groups as well as similar, known protective groups are split off in a fashion more or less generally known.

Particularly preferred embodiments of the invention result from following examples and the Patent Claims.

EXAMPLE 1

Catalpol (1a) from Picrorhiza kurrooa: Add 10 kg of the ground drug of Picrorhiza kurrooa to 100 kg of 5% soda solution and heat at 93°–95° C. for 3 hours by feeding in steam. Condensation of steam through the drug causes it to be whirled about, thus providing a good extraction. Filter through a perlon cloth overnight and extract the residue once more with 80 kg of 5% soda solution. Combine the filtrates and maintain at boiling heat for 20 minutes, then mix with 10 kg activated charcoal for 3 hours at 80° C. Leave the charcoal to settle overnight. Treat the decanted solution once more with 4 kg activated charcoal. Suck off the combined charcoal through an earthenware suction filter with a diameter of 60 cm with has previously been given a sediment layer of approx. 2 kg "Hyflo-Super-Cel"; then wash with water until the filtrate indicates a pH value of approx. 8. The air dried charcoal is boiled up three times, each time using 50 kg of 95% ethanol. After sucking off, approx. 166 kg solution is obtained which is initially concentrated in a distillery down to approx. 30 kg, and then reduced to dryness in a 100 liter rotary evaporator. Subsequent lyophilization results in a dark brown catalpol-concentrate containing still appreciable quantities of sugar and a little picroside mixture; yield: 1570 g (14.5% in relation to dried drug).

Add 300 g $Al_2O_3$ (neutral, activity grade I) and 1.5 liter ethanol to 250 g of the catalpol concentrate. Mixing all the time, heat up to boiling and distill off 1.0 liter ethanol. This mixture is put onto an $Al_2O_3$ column (100×5 cm; 1200 g $Al_2O_3$ washed with ethanol) and eluated with a (9:1) mixture of ethanol and water. The fractions containing the catalpol are detected by thin-layer chromatographic evaluation (TLC: Rf=0.34; Solvent: $CHCl_3/CH_3OH/2N$ $CH_3COOH$ 70:30:6) and combined. Evaporate the solution entirely in a vacuum at an immersion temperature of 52° C. to dryness. The foam initially produced is crystallized from ethanol. Suck off the crystals and wash well with ethanol. By means of column-chromatographic separation of the mother liquor via an $Al_2O_3$ column it is possible to isolate a further quantity of catalpol.

Catalpol (1a), $C_{15}H_{22}O_{10}$ (362.3), yield 45 g (18% in relation to catalpol concentrate), melting point 202°–204° C., $[\alpha]_{589}^{20}=-39.7°$ (c=1.2 g in 100 ml ethanol).

1st reaction step: Dissolve 15 g catalpol (1a) in 24 ml absolute pyridine at room temperature and add 30 ml acetic anhydride. Let the reaction solution stand for 15 hours at room temperature and subsequently pour into ice water. Knead the precipitated product until it assumes a solid form and can be filtered with suction. Wash the amorphous product with ice water, dry and recrystallize with a little ethanol.

Hexaacetyl-catalpol (1b), $C_{27}H_{34}O_{16}$ (614.6), yield 22 g (86%), melting point 142°–143° C., $[\alpha]_{589}^{20}=-87.3°$ (c=1 g in 100 ml $CHCl_3$), Rf=0.34 (Solvent: benzene/acetone 8:2).

2nd reaction step: Dissolve 22 g hexaacetyl-catalpol (1b) in approximately 50 ml acetic ester and add 1.5 g Pd/C catalyst (10% Pd). Hydrogenate in the appropriate apparatus until no more hydrogen is absorbed (approx. 970 ml $H_2$ within approx. 2 hours; calc. 802 ml $H_2$). Filter off the catalyst and reduce the filtrate to dryness in vacuum (immersion temp. 45° C.) by evaporation.

Recrystallize the residue with a little ethanol.

Hexaacetyl-dihydrocatalpol (2b), $C_{27}H_{36}O_{16}$ (616.6), yield 22 g (99%), Melting Point 155°–156° C., $[\alpha]_{589}^{20}=-80.4°$ (c=1 g in 100 ml $CHCl_3$), Rf=0.30 (benzene/acetone 8:2).

3rd reaction step: Add, in small portions, 18.4 g (30 mmole) hexaacetyl-dihydrocatalpol (2b) to a suspension of 7.4 g (195 mmole) $LiAlH_4$ in 1000 ml anhydrous tetrahydrofuran (THF), and boil for 4 hours under constant stirring and with reflux condensation. Decompose the surplus $LiAlH_4$ with acetic ester and water. After introduction of $CO_2$, filter off the inorganic salts and wash the residue a number of times with water. Evaporate the THF in vacuum at an immersion temperature of 40° C. and heat the aqueous solution for three hours at 80° C. with 50 g activated charcoal (use stirrer). After decanting from the settled charcoal, treat the solution twice again, using 50 g activated charcoal each time. Thin-layer Chromatography is used to show that no more 3a is present in the aqueous solution. Suck off the charcoal and wash with water until no more inorganic salts can be detected. After air drying the carbon, extract it several times using 95% ethanol at boiling heat for 10 minutes. Reduce the collected filtrates to dryness in vacuum.

6,8-dihydroxy-8-(hydroxymethyl)-1-iridanyl-1'-β-D-glucopyranoside (3a), $C_{15}H_{26}O_{10}$ (366.4), yield 9.5 g (86%), amorphous $[\alpha]_{589}^{20}=-77.1°$ (c=1.9 g in 100 ml $CH_3OH$). Rf=0.27 ($CHCl_3/CH_3OH/2N$ $CH_3COOH$ 60:50:6).

4th reaction step: Add 15 g (70 mmole) of sodium periodate to a solution of 5.5 g (15 mmole) 3a in 250 ml water. Allow the solution to stand at room temperature for half an hour, shaking from time to time. After adding 20 g sodium hydrogen carbonate (pH=8), filter off the inorganic salts and wash with 50 ml water. Reduce the filtrate by evaporation under vacuum at 35° C. immersion temperature until further inorganic salts start precipitating. Extract the colourless solution five times, using 100 ml acetic ester in each case. The acetic ester is dried with sodium sulphate and completely evaporated in vacuum at an immersion temperature of 35° C. The oil initially obtained crystallizes when subjected to rubbing. For analysis, dissolve the product in very little cold dioxane and add carbon tetrachloride to opacity. The substance 4a crystallizes out in the refrigerator.

(6R, 7R)-(−)-7-hydroxy-3-oxa-bicyclo[4.3.0]non-1-en -9-one (4a), $C_8H_{10}O_3$ (154.2), yield 1.8 g (78%), Melting Point 95°–97° C., $[\alpha]_{589}^{20}=-267°$ (c=3 g in 100 ml $CH_3OH$), Rf=0.32 ($CHCl_3/CH_3OH$ 9:1)

Application of the Compounds according to the Invention for the Synthesis of Prostanoids 1st reaction step: Add, one after the other, 2 ml benzyl mercaptane and 0.2 ml triethylamine to a solution of 1.6 g (10.4 mmole) ketoenolether (4a) in 3 ml THF. Stir for 5 hours at room temperature. Evaporate the reaction solution of dryness in vacuum. Recrystallize the residue out of carbon tetrachloride.

1-(benzylthio)-7-hydroxy-3-oxa-bicyclo[4.3.0]nonanone (5a), $C_{15}H_{18}O_3S$ (278.3), yield 2.3 g (79.6%), Melting Point 118° C., $[\alpha]_{589}^{20}=-188°$ (c=2 g in 100 ml $CHCl_3$), Rf=0.23 (benzene/acetone 8:2).

2nd reaction step: At a temperature of −15° C. to −20° C., add dropwise a solution of 1.95 g (7 mmole) of the substance 5a in 20 ml absolute methanol to a solution of 265 mg (7 mmole) NaBH₄ in 20 ml absolute methanol within a period of approx. half an hour. Stir for four hours at a temperature of −15° C. Remove the cooling bath and allow the solution to warm up to room temperature by introducing carbon dioxide. During this process, add 50 ml water in drops. Shake out the reaction solution five times, using 50 ml ether each time. Dry the ether with anhydrous sodium sulphate and evaporate to dryness in vacuum. Then pass the residue through a pressure column measuring 80×2 cm filled with silica gel using, one after the other, 300 ml benzene, 1600 ml benzene/acetone (95:5) and 1600 ml benzene/acetone (90:10) and 1000 ml benzene/acetone (80:20). Determine the fractions by means of thin layer chromatography using a chloroform/methanol mixture (9:1) as solvent.

(7R, 9S)-(−)-1-(benzylthio)-7,9-dihydroxy-3-oxa-bicyclo-[4.3.0]nonane (6a), $C_{15}H_{20}O_3S$ (280.3), yield 1.13 g (57.6%), oil $[\alpha]_{589}^{20} = -340°$ (c=1.6 g in 100 ml acetone), Rf=0.38 ($CHCl_3/CH_3OH$ 9:1).

(7R, 9R)-(−)-1-(benzylthio)-7,9-dihydroxy-3-oxa-bicyclo[4.3.0]nonane (6b), $C_{15}H_{20}O_3S$ (280.3), yield 295 mg (15%), crystals from carbon tetrachloride, Melting Point 78°–79° C., $[\alpha]_{589}^{20} = -154.9°$ (c=2 g in 100 ml acetone), Rf=0.32 ($CHCl_3/CH_3OH$ 9:1).

3rd reaction step: Over a period of 3 minutes, add a solution of 280 mg (1 mmole) of the substance 6a or of the substance 6b in 3.5 ml acetonitrile dropwise to a solution of 175 mg (0.55 mmole) mercury acetate in 3.5 ml water. Stir for 10 minutes and dilute with 15 ml water. After filtration of the solution, reduce it to dryness by evaporating in vacuum. Purify the residue via a pressure column measuring 80×1 cm containing silica gel with a 9:1 mixture of chloroform/methanol.

(7R, 9S)-(−)-2,7,9-trihydroxy-3-oxa-bicyclo[4.3.0]nonane (7a), $C_8H_{14}O_4$ (174.2), yield 80%, oil, specific rotation not yet determined, Rf=0.24 ($CHCl_3/CH_3OH$ 8:2).

(7R, 9R)-(−)-2,7,9-trihydroxy-3-oxa-bicyclo[4.3.0]nonane (7b) $C_8H_{14}O_4$ (174.2), crystals from a little acetone, yield 84%, Melting Point 108°–110° C., $[\alpha]_{589}^{20} = -21.7°$ (c=1 g in 100 ml methanol), Rf=0.22, ($CHCl_3/CH_3OH$ 8:2).

4th reaction step: Dissolve 1.3 g (4.7 mmole) of the substance 5a with 3.7 g (14 mmole) triphenylphosphine and 1.15 g (9.4 mmole) benzoic acid in 60 ml absolute benzene. With stirring, add in the form of drops a solution of 1.64 g (9.4 mmole) diethyl azodicarboxylate in benzene at room temperature (introducing the drops at a rate of one every three seconds). During the reaction, a white precipitate consisting of diethyl hydrazodicarboxylate is formed. As soon as the reaction solution assumes a weak yellow colour, terminate the reaction. By means of thin-layer chromatography no more initial substance can be detected. Remove the precipitate by suction and attach the precipitate to "Celite". Purify the substance via a pressure column measuring 80×2 cm with silica gel using a 95:5 mixture of benzene/acetone.

(6R,7S)-1-(benzylthio)-7-(benzoyloxy)-3-oxa-bicyclo[4.3.0]nonane -9-one (5b); R=benzoyl—) $C_{15}H_{18}O_5$ (278.3), yield 1.3 g (56%), oil, Rf=0.52 (benzene/acetone 8:2). The Rf value of 5b (R=benzoyl—) is different to that of 5a (R=benzoyl—) (Rf=0.64 in the same solvent). The product has not been examined further. By means of saponification, it should be possible to obtain 5b (R=H).

5th through 8th reaction steps: Further processing of the compounds 7a, 7b, 7c and 7d to prostanoids 11 is performed as described above (comp. p. 9 above).

We claim:

1. Iridoid derivatives of the general formula I,

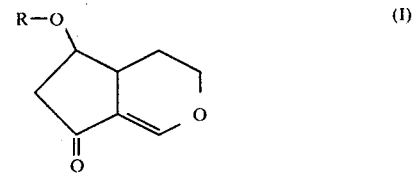

wherein R is a hydrogen atom, an alkyl group with 1 to 5 carbon atoms, an alkanoyl group with 2 to 6 carbon atoms, a non-substituted aralkyl group with 7 to 12 carbon atoms, a methanesulfonyl group, or a toluenesulfonyl- group, a benzoyl group, a para-substituted nitrobenzoyl group chlorobenzoyl group or a tetrahydropyranyl-group.

2. 7-hydroxy-3-oxa-bicyclo[4.3.0]non-1-en -9-one.

3. (6R,7R)-(−)-7-hydroxy-3-oxa-bicyclo[4.3.0]-non-1-en -9-one.

4. 7-acetoxy-3-oxa-bicyclo[4.3.0]non-1-en -9-one.

* * * * *